US010261001B2

(12) United States Patent
Willis et al.

(10) Patent No.: US 10,261,001 B2
(45) Date of Patent: Apr. 16, 2019

(54) MANUALLY OPERATED DESORBER FOR SENSOR DETECTOR DEVICE

(71) Applicant: FLIR Detection, Inc., Stillwater, OK (US)

(72) Inventors: Chris Willis, Stillwater, OK (US); Matthew Szabo, Stillwater, OK (US); Craig Aker, Stillwater, OK (US)

(73) Assignee: FLIR DETECTION, INC., Stillwater, OK (US)

(*) Notice: Subject to any disclaimer, the term of this patent is extended or adjusted under 35 U.S.C. 154(b) by 172 days.

(21) Appl. No.: 15/296,974

(22) Filed: Oct. 18, 2016

(65) Prior Publication Data
US 2017/0115193 A1 Apr. 27, 2017

Related U.S. Application Data

(60) Provisional application No. 62/244,370, filed on Oct. 21, 2015.

(51) Int. Cl.
G01N 30/00 (2006.01)
G01N 1/44 (2006.01)
G01N 1/10 (2006.01)
G01N 1/02 (2006.01)

(52) U.S. Cl.
CPC .............. G01N 1/44 (2013.01); G01N 1/10 (2013.01); G01N 30/00 (2013.01); G01N 2001/022 (2013.01); G01N 2001/028 (2013.01)

(58) Field of Classification Search
CPC .......... G01F 1/684; G01F 1/6842; G01F 1/68; G01F 5/00; G01F 1/6845
USPC ..... 73/863.12, 54.42, 61.74, 152.12, 861.95, 73/202.5, 204.11
See application file for complete search history.

(56) References Cited

U.S. PATENT DOCUMENTS

| 3,535,939 | A | * | 10/1970 | Dobbs | G01N 30/20 251/62 |
| 6,558,626 | B1 | | 5/2003 | Aker et al. | |
| 7,419,636 | B2 | | 9/2008 | Aker et al. | |
| 8,323,576 | B2 | | 12/2012 | Aker et al. | |
| 8,675,127 | B2 | * | 3/2014 | Nakajima | H04N 5/2253 348/359 |
| 9,921,385 | B2 | * | 3/2018 | Willis | G02B 7/02 |
| 2003/0115949 | A1 | * | 6/2003 | Ambrosina | G01F 1/684 73/202.5 |

(Continued)

FOREIGN PATENT DOCUMENTS

WO    WO 2015/054583    4/2015

Primary Examiner — Natalie Huls
Assistant Examiner — Mohammed E Keramet-Amircolai
(74) Attorney, Agent, or Firm — Haynes and Boone, LLP

(57) ABSTRACT

Various techniques are provided to implement a desorber of a sensor detector device that permits manual operation and is completely detachable from a main body of the sensor detector device. In one example, a device includes a desorber. The desorber includes an inlet comprising a fluid path configured to receive samples vaporized from sample media. The desorber also includes a cap configured to slide toward the inlet in response to a manual actuation of the cap performed by a user to transition the desorber from an open position to a closed position. The desorber further includes a heater configured to slide with the cap toward the inlet in response to the user actuation and vaporize the samples while the desorber is in the closed position.

19 Claims, 17 Drawing Sheets

(56) References Cited

U.S. PATENT DOCUMENTS

| | | | | |
|---|---|---|---|---|
| 2007/0277585 A1* | 12/2007 | Szabo | ............... | G01N 1/28 |
| | | | | 73/1.05 |
| 2009/0007573 A1* | 1/2009 | Noonan | ............ | F25B 17/08 |
| | | | | 62/51.1 |
| 2009/0166511 A1* | 7/2009 | Kwon | ............... | G01J 1/02 |
| | | | | 250/206 |
| 2012/0092543 A1* | 4/2012 | Afshari | ............ | H04N 5/2254 |
| | | | | 348/335 |
| 2012/0140101 A1* | 6/2012 | Afshari | ............ | H04N 5/2257 |
| | | | | 348/308 |
| 2012/0218450 A1* | 8/2012 | Pavithran | ......... | H04N 5/2254 |
| | | | | 348/296 |
| 2012/0304729 A1* | 12/2012 | O'Dell | ............ | G01N 21/77 |
| | | | | 73/1.02 |
| 2013/0057757 A1* | 3/2013 | Ryou | ............... | G02B 7/08 |
| | | | | 348/374 |
| 2014/0041437 A1* | 2/2014 | Hedtke | ............ | G01L 9/0075 |
| | | | | 73/1.57 |
| 2014/0065720 A1* | 3/2014 | Ja | ............... | G01N 21/6428 |
| | | | | 436/172 |
| 2017/0023453 A1* | 1/2017 | Hill, Jr. | ............ | G01N 1/4022 |

* cited by examiner

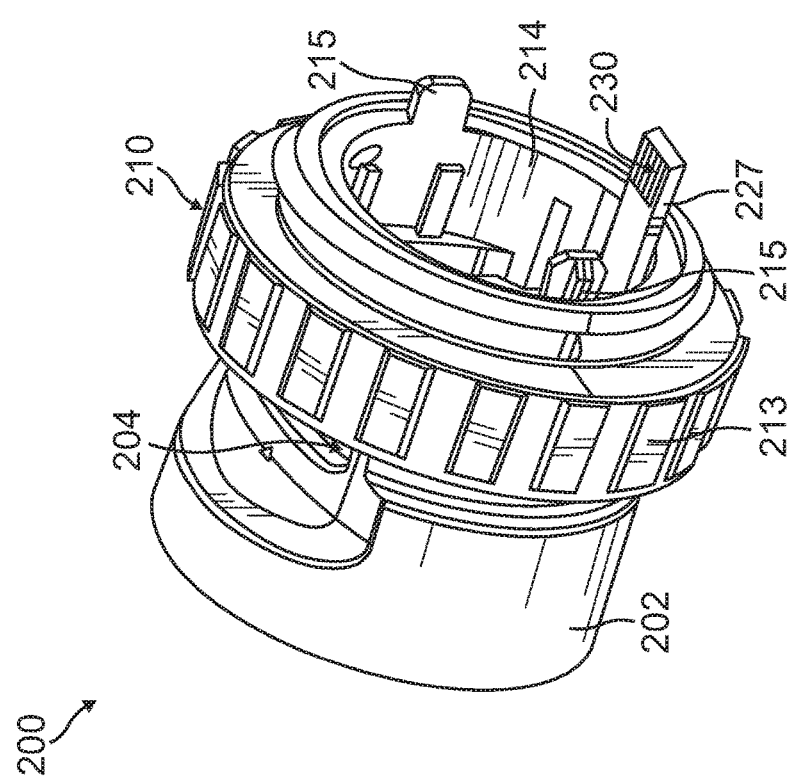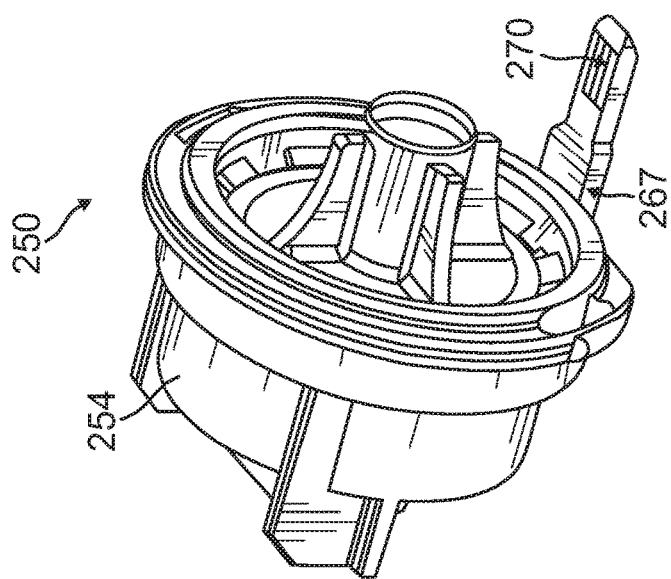
FIG. 8

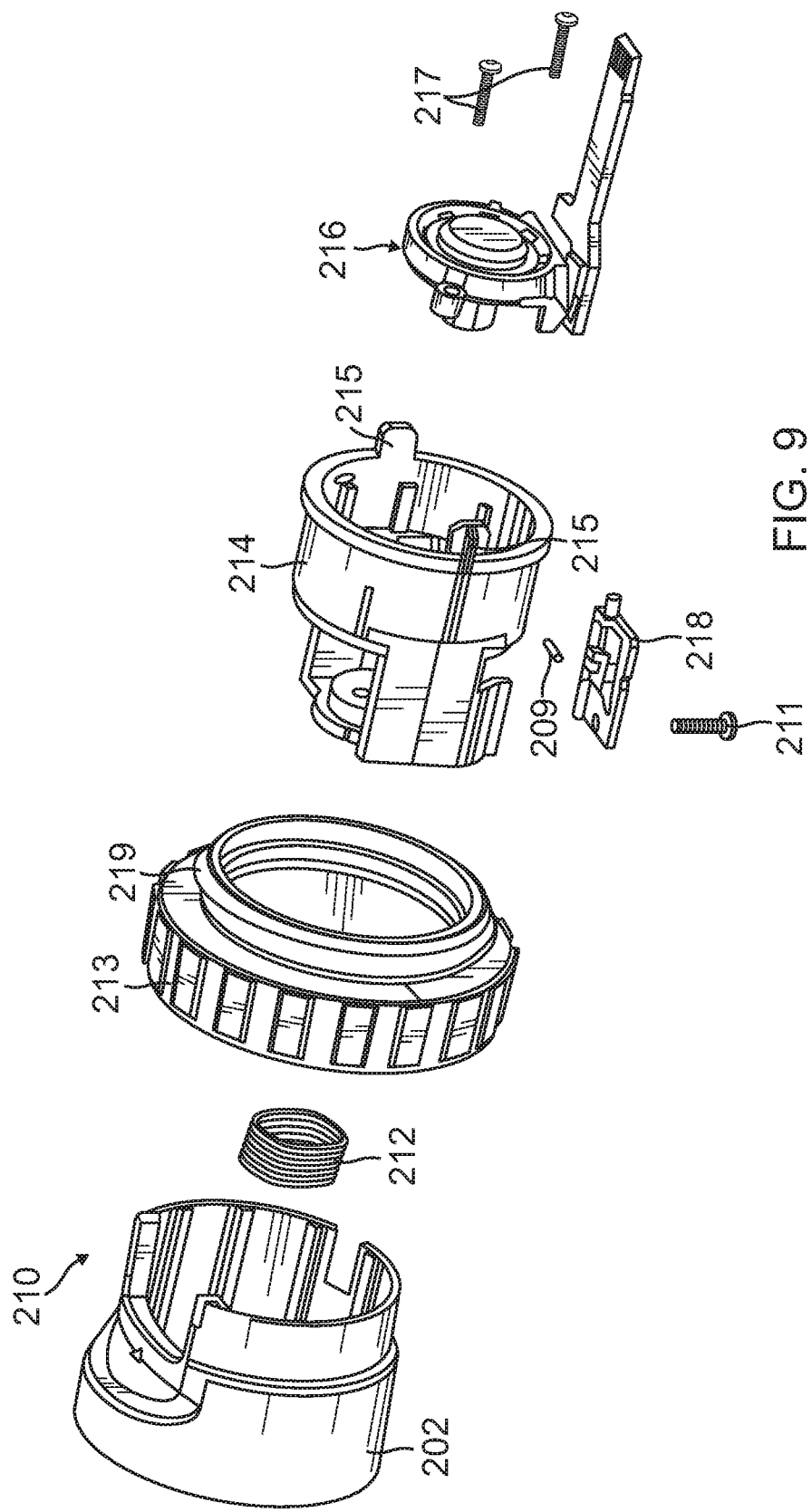

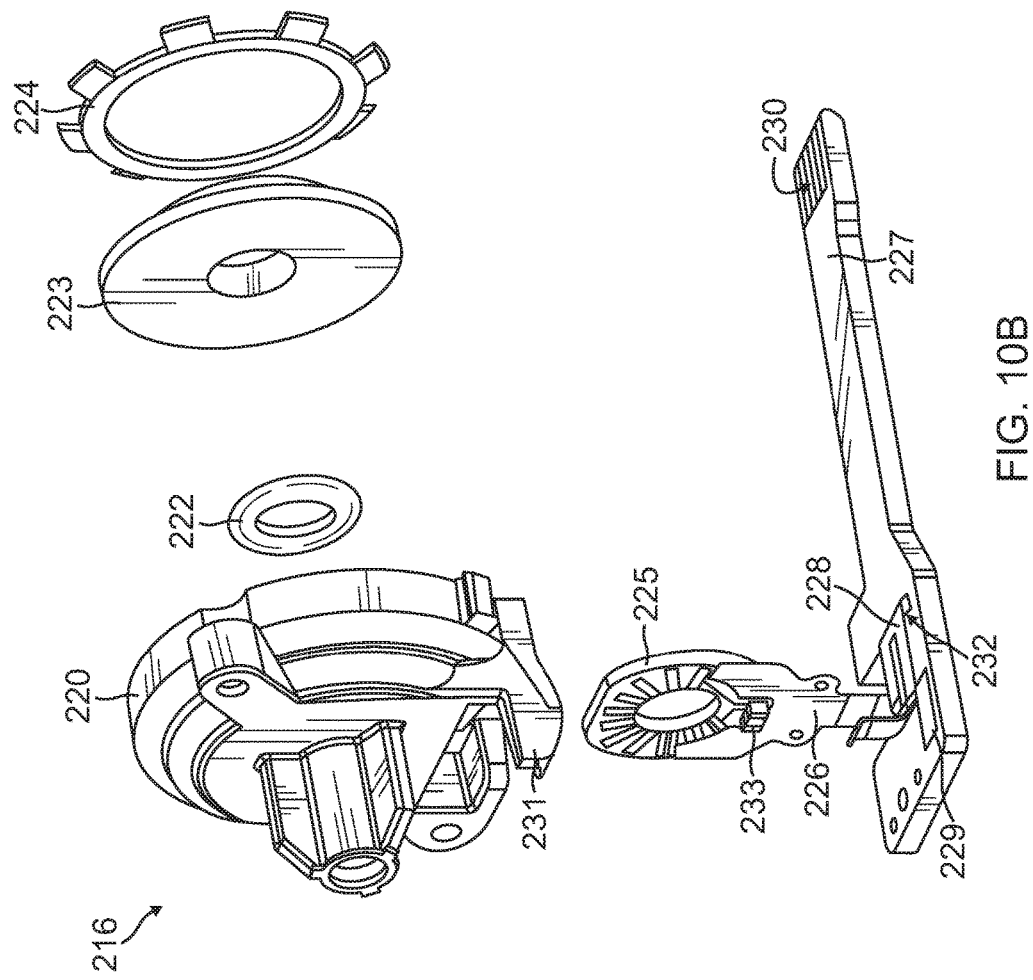

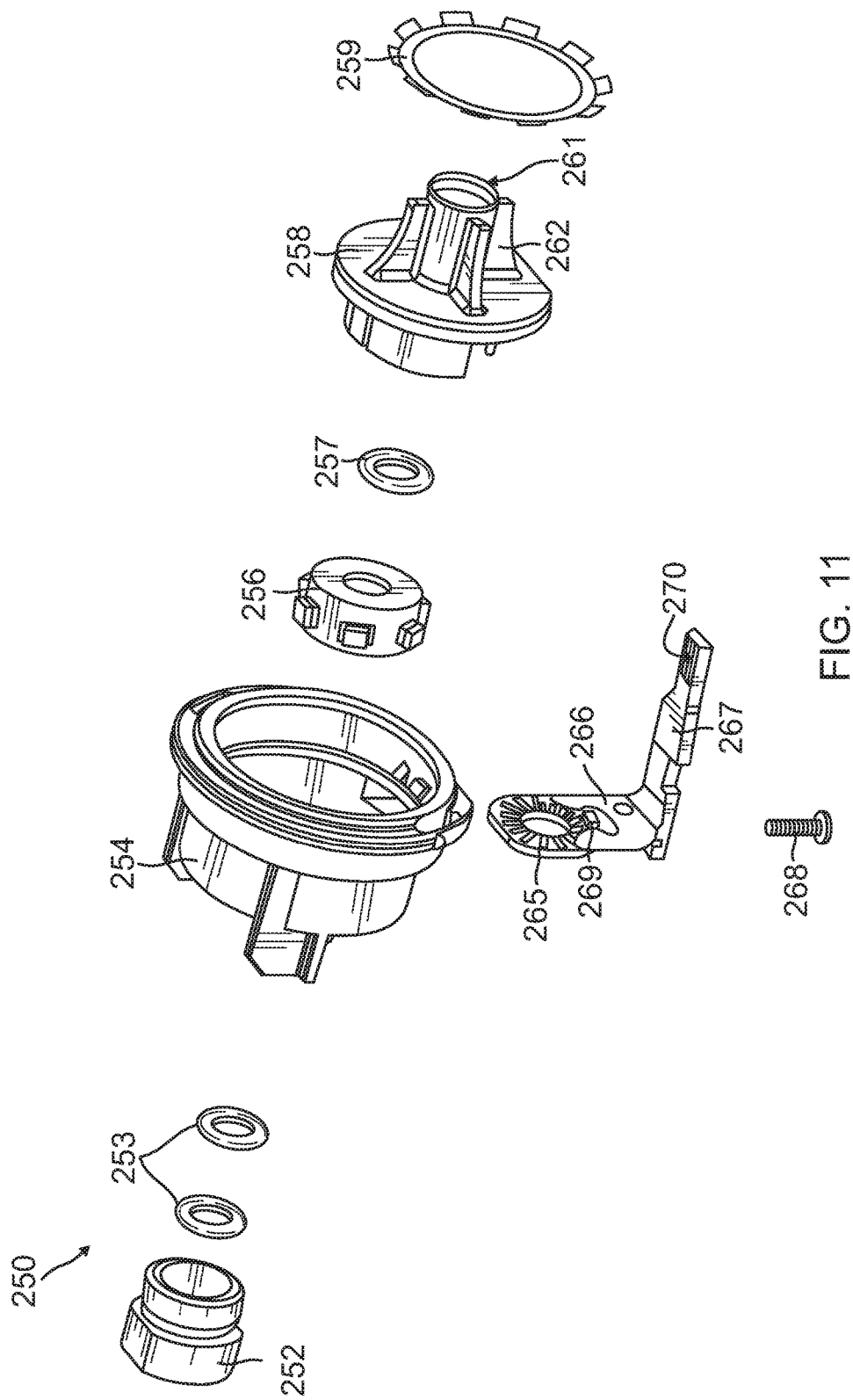

MANUALLY OPERATED DESORBER FOR SENSOR DETECTOR DEVICE

CROSS-REFERENCE TO RELATED APPLICATIONS

This application claims priority to and the benefit of U.S. Provisional Patent Application No. 62/244,370, filed Oct. 21, 2015 and entitled "MANUALLY OPERATED DESORBER FOR SENSOR DETECTOR DEVICE," which is hereby incorporated by reference in its entirety.

TECHNICAL FIELD

The present invention relates generally to chemical detection devices and, more particularly, to mobile user controlled sensor detector devices.

BACKGROUND

Various types of sensor detector devices are used to analyze chemical samples for traces of explosive materials or other substances. In particular, some such devices are designed for portable use in the field, such as handheld use.

In practice, some of these devices rely on complex automated mechanisms to physically move various components to capture and analyze samples. Although sometimes useful, these automated implementations can add weight and thus limit the portability of such devices. In addition, such implementations can prevent the user from directly starting, stopping, or pausing various operations. Instead, such devices typically require the user to indirectly control desorber operations through various types of software controls.

Moreover, the above-mentioned automated mechanisms may be embedded within the sensor detector device itself and may not be readily serviceable in the field. In particular, if one or more of the automated mechanisms fails, it may not be possible for a user to actually repair the automated mechanism or restore the device to full working order while in the field.

Routine servicing of such devices can also be unduly burdensome, as significant disassembly may be required to access components to be serviced. These various problems can reduce the reliability and overall usefulness of such devices.

SUMMARY

In accordance with various embodiments further discussed herein, a desorber of a sensor detector device may be implemented in a manner that permits manual operation, thus permitting direct user control of the desorber and reducing cost and weight. The desorber may be completely detached from a main body of the sensor detector device for convenient and flexible servicing. These and many other features may be provided in various combinations as desired and as more fully discussed herein.

In one embodiment, a device includes a desorber comprising: an inlet comprising a fluid path configured to receive samples vaporized from sample media; a cap configured to slide toward the inlet in response to a manual actuation of the cap performed by a user to transition the desorber from an open position to a closed position; and a heater configured to slide with the cap toward the inlet in response to the user actuation and vaporize the samples while the desorber is in the closed position.

In another embodiment, a method includes providing a sensor detector device comprising a main body and a desorber, wherein the desorber is configured to be selectively attached to the main body, wherein the desorber comprises a cap, an inlet, and a heater; receiving sample media in the desorber; receiving a manual actuation of the cap performed by a user to transition the desorber from an open position to a closed position; sliding the cap and the heater toward the inlet in response to the user actuation; vaporizing samples from the sample media by the heater; and passing the vaporized samples through a fluid path of the inlet.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIG. 8 is a perspective view of a desorber having a main assembly separated from an inlet subassembly in accordance with an embodiment of the disclosure.

FIG. 9 is an exploded view of a desorber main assembly in accordance with an embodiment of the disclosure.

FIGS. 10A-B are several exploded views of a slidable member subassembly in accordance with an embodiment of the disclosure.

FIG. 11 is an exploded view of a desorber inlet subassembly in accordance with an embodiment of the disclosure.

Embodiments of the present invention and their advantages are best understood by referring to the detailed description that follows. It should be appreciated that like reference numerals are used to identify like elements illustrated in one or more of the figures.

DETAILED DESCRIPTION

In accordance with various embodiments provided herein, a sensor detector device (e.g., also referred to as a mobile detection device) is provided with a manually operated desorber. By implementing the desorber for manual operation, the desorber may be implemented without electric motors, solenoids, or electro-mechanical drives, thus saving weight and cost. Moreover, manual operation permits a user to retain continuous control over the engagement of the desorber with sample media. In this regard, a user may selectively actuate or release the desorber so as to immediately start, stop, or interrupt a chemical analysis process as desired. In particular, the desorber may be spring loaded and implemented with a compression spring sufficient to overcome dirt, dust, or other debris that may enter the desorber.

In various embodiments, the sensor detector device may be implemented in a modular fashion such that the desorber may be selectively attached to, and detached from, a main body of the sensor detector device by the user with minimal effort and without requiring tools or any significant disassembly of the main body of the sensor detector device. For example, the desorber may be attached externally to the main body by screw threads and may be easily detached therefrom for convenient cleaning, servicing, replacement, transport, or other operations. In some embodiments, such threads may be implemented as right-handed double-helix buttress threads to maintain a reliable alignment of the desorber with a detector and other related components in the main body of the sensor detector device.

In various embodiments, the desorber may be assembled with various fasteners and mechanical engagements, and without the use of adhesives or other techniques that might limit an end user's ability to rapidly service the desorber. Moreover, the various components used to implement the desorber may be implemented without adhesives, low temperature plastics, or other materials that would otherwise melt or outgas when heated to prevent contamination of samples processed by the sensor detector and to ensure the user is thermally insulated from heated components.

Figure 1:
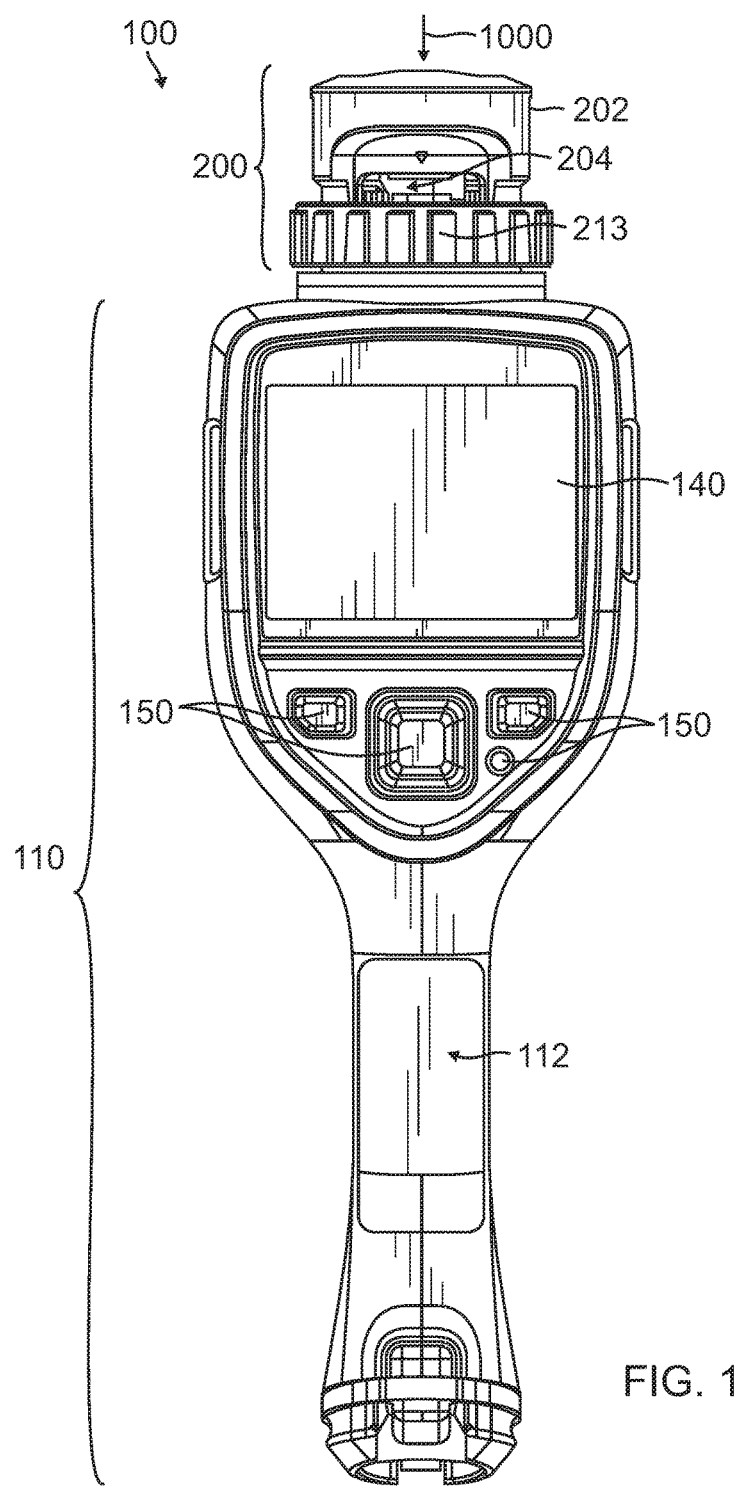
FIG. 1 is a front view of a sensor detector device in accordance with an embodiment of the disclosure.

FIG. 1 is a front view of a sensor detector device 100 in accordance with an embodiment of the disclosure. For example, device 100 may be implemented as a handheld portable chemical detector capable of detecting explosives, chemical warfare agents, biological warfare agents, and/or hazardous chemicals materials and/or other substances.

As shown, device 100 includes a main body 110 and a desorber 200 that may be selectively attached thereto. Main body 110 includes a housing 112 (e.g., a handheld housing having an integrated handle to permit convenient portable use of device 100 in the field), a screen 140, user controls 150, and additional components further discussed herein.

Desorber 200 includes a user operable cap 202, a chamber 204 (e.g., visible as an open slot in FIG. 1), a threaded ring 213, and additional components further discussed herein. Cap 202 is configured to depress (e.g., slide) toward threaded ring 213 and main body 110 in response to a user actuation in the direction of arrow 1000. Sample media disposed in chamber 204 may be captured, sampled, and analyzed in response to such user actuation as further discussed herein.

Figure 2:
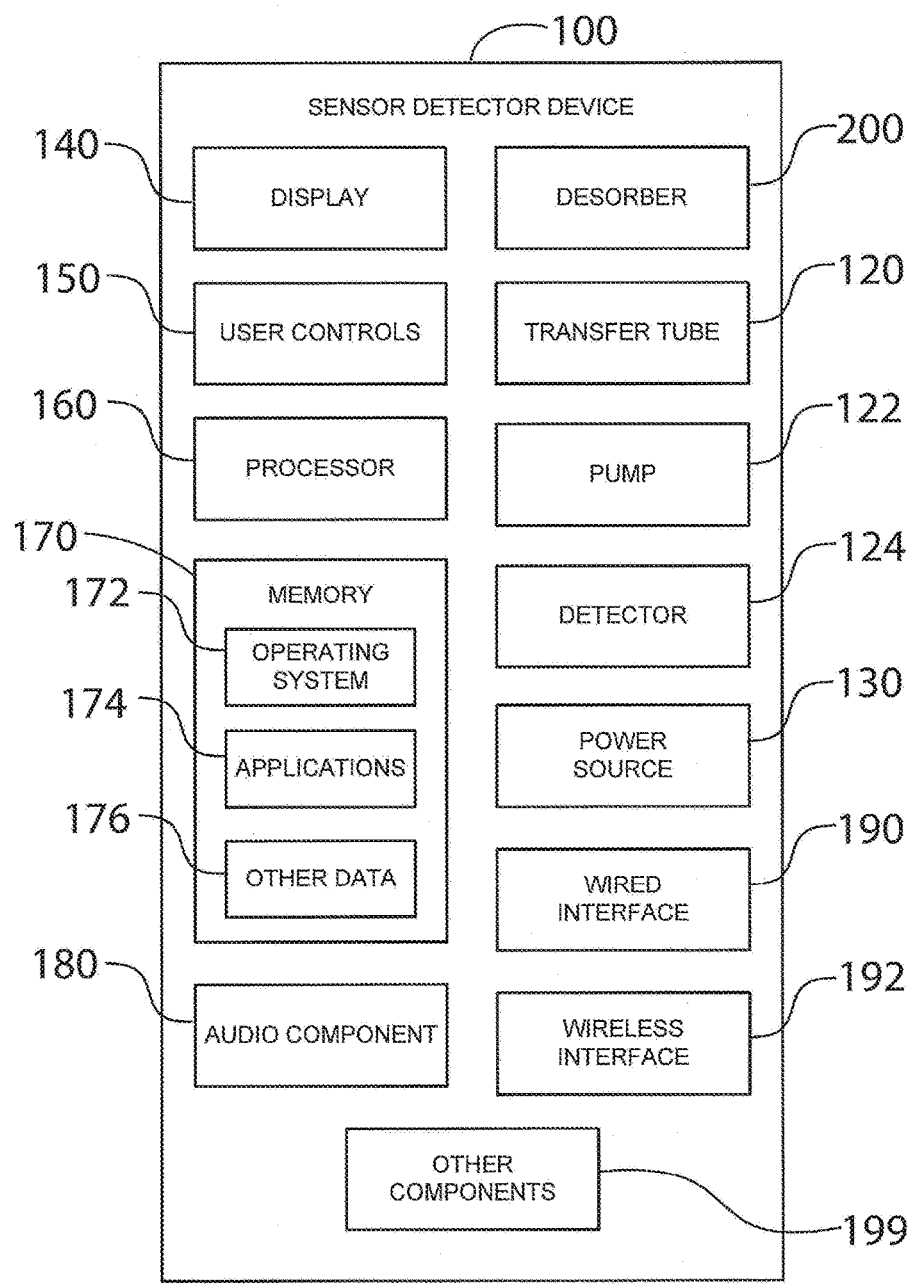
FIG. 2 is a block diagram of a sensor detector device in accordance with an embodiment of the disclosure.

FIG. 2 is a block diagram of device 100 in accordance with an embodiment of the disclosure. As identified in FIG. 2, device 100 includes a desorber 200, a transfer tube 120, a pump 122, a detector 124, a power source 130, a display 140, user controls 150, a processor 160, a memory 170, an audio component 180, a wired interface 190, a wireless interface 192, and other components 199. Although a variety of components are illustrated in the block diagram of FIG. 2, various components may be added and/or omitted as appropriate in various embodiments.

As will be further discussed herein, desorber 200 receives sample media and vaporizes samples (e.g., particles corresponding to various chemicals) disposed thereon. The vaporized samples are passed from desorber 200 through transfer tube 120 to detector 124. For example, in some embodiments, pump 122 may introduce a vacuum in transfer tube 120 to draw the vaporized samples toward detector 124. The samples received by detector 124 (e.g., also referred to as analytes) are analyzed to detect the presence of various chemicals of interest. Detector 124 may be implemented in accordance with any desired chemical detection process. For example, in some embodiments, detector 124 may be implemented in accordance with any of the techniques identified in U.S. Pat. Nos. 6,558,626, 7,419,636, and 8,323,576, and U.S. Patent Application Publication No. 2012/0304729, all of which are hereby incorporated by reference herein in their entirety.

Power source 130 may be implemented, for example, as one or more batteries to permit mobile and remote use of device 100. In some embodiments, power source 130 may be one or more removable batteries.

Display 140 presents information to the user of device 100. In various embodiments, display may be implemented as a liquid crystal display (LCD), an organic light emitting diode (OLED) display, and/or any other appropriate display.

User controls 150 receive user input to operate various features of device 100. As shown in FIG. 1, user controls 150 may be implemented as physical buttons. In other embodiments, user controls 150 may be implemented by one or more keyboards, levers, joysticks, and/or other controls. In some embodiments, user controls 150 may be integrated with display 140 as a touchscreen.

Processor 160 may be implemented as one or more microprocessors, microcontrollers, application specific integrated circuits (ASICs), programmable logic devices (PLDs) (e.g., field programmable gate arrays (FPGAs), complex programmable logic devices (CPLDs), field programmable systems on a chip (FPSCs), or other types of programmable devices), or other processing devices used to control the operations of device 100. In this regard, processor 160 may execute machine readable instructions (e.g., software, firmware, or other instructions) stored in memory 170.

Memory 170 may be implemented as a machine readable medium storing various machine readable instructions and data. For example, in some embodiments, memory 170 may store an operating system 172 and one or more applications 174 as machine readable instructions that may be read and executed by processor 160 to perform various operations described herein. Memory 170 may also store various other data 176, such the results of one or more chemical analysis processes and/or other information as appropriate. In some embodiments, memory 170 may be implemented as non-volatile memory (e.g., flash memory, hard drive, solid state drive, or others), volatile memory, or combinations thereof.

Audio component 180 may be implemented, for example, as a speaker or other transducer with corresponding driver circuitry to provide audible sounds to a user of device 100.

For example, in some embodiments, audio component 180 may provide audible signals such as audible feedback to the user in response to manipulation of cap 202, manipulation of user controls 150, and/or in response to the operations of desorber 200, detector 124, processor 160, and/or any of the various components of device 100.

Wired interface 190 may be implemented as one or more physical interfaces (e.g., by Universal Serial Bus (USB), Ethernet, and/or other protocols) configured to connect device 100 with various external devices for wired communications. In particular, wired interface 190 may be used to download data and/or to connect to power sources (e.g., a power outlet) to charge one or more batteries of power source 130 and/or to directly power device 100.

Wireless interface 192 may be implemented as one or more WiFi, Bluetooth, cellular, infrared, radio, and/or other types of interfaces for wireless communications to download data in the manner described for wired interface 190. Other components 199 may also be provided as appropriate to support, for example, application specific operations of device 100.

Figure 3:
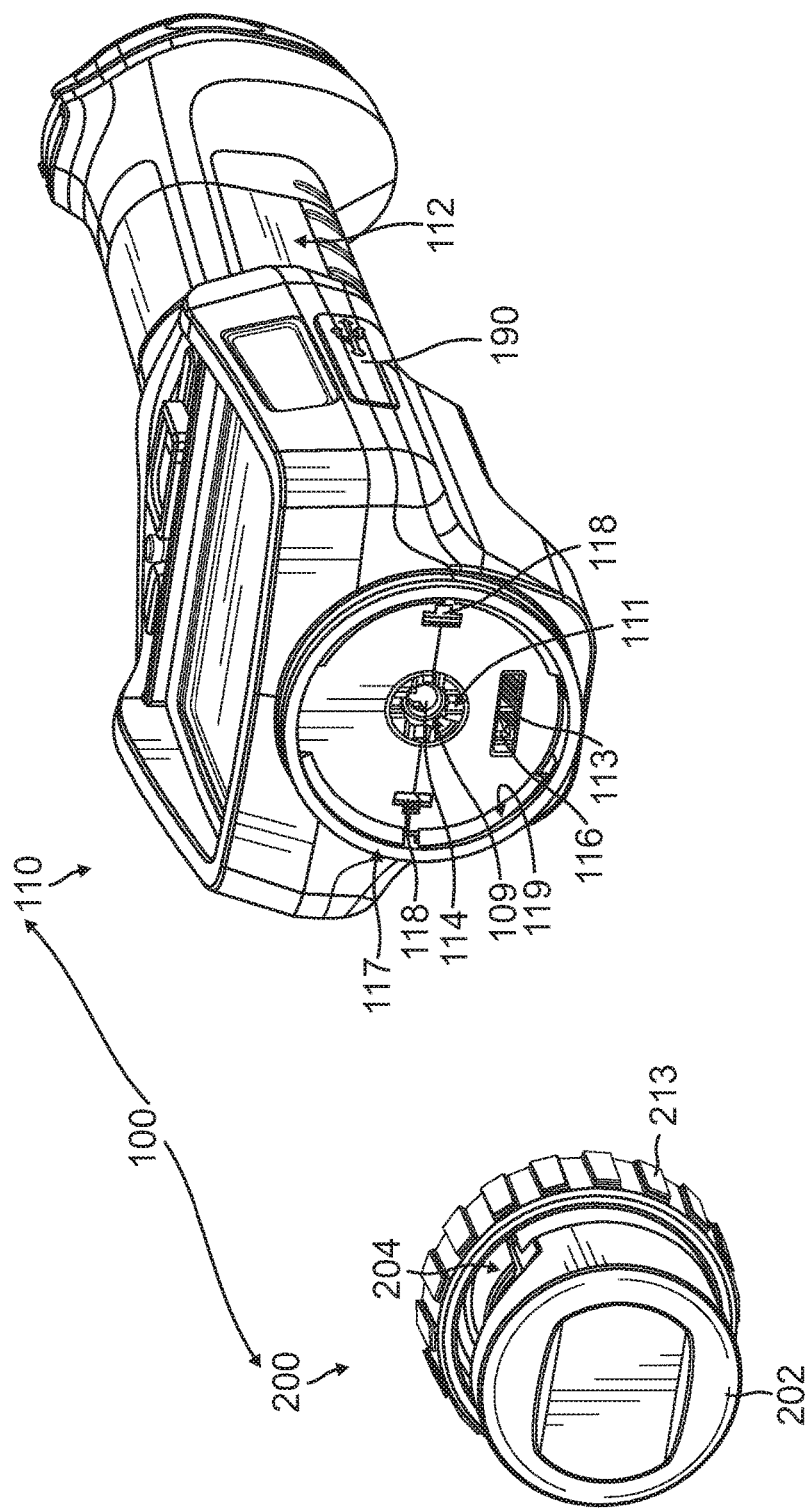
FIG. 3 is a perspective view of a sensor detector device having a desorber detached therefrom in accordance with an embodiment of the disclosure.

FIG. 3 is a perspective view of device 100 having desorber 200 detached from main body 110 in accordance with an embodiment of the disclosure. As shown, main body 110 includes an aperture 117 having threads 119 disposed on an inside surface thereof. In this regard, threads 119 may engage with complementary threads 219 (see FIG. 4) of threaded ring 213. As discussed, in some embodiments, threads 119 and 219 may be implemented as right handed double helix buttress threads for convenient attachment and detachment by the user.

Main body 110 also includes a cavity 114 in fluid communication with detector 124 and configured to receive transfer tube 120. Main body 110 further includes electrical connections 113/116 configured to receive complementary electrical connections 230/270 from circuit boards 227/267 of desorber 200 (see FIG. 6) to connect various electrical components of desorber 200 to detector 124, power source 130, processor 160, and/or various components of main body 110 through appropriate conductive paths provided by one or more circuit boards of main body 110. Main body 110 also includes apertures 118 configured to receive complementary flanges 215 (see FIG. 6) of desorber 200 to physically align desorber 200 with main body 110. Main body 110 also includes recesses 109 and 111 configured to receive a front surface 261 and flanges 262, respectively of a retainer 258 of desorber 200 (see FIG. 11) to further physically align desorber 200 with main body 110.

Figure 4:
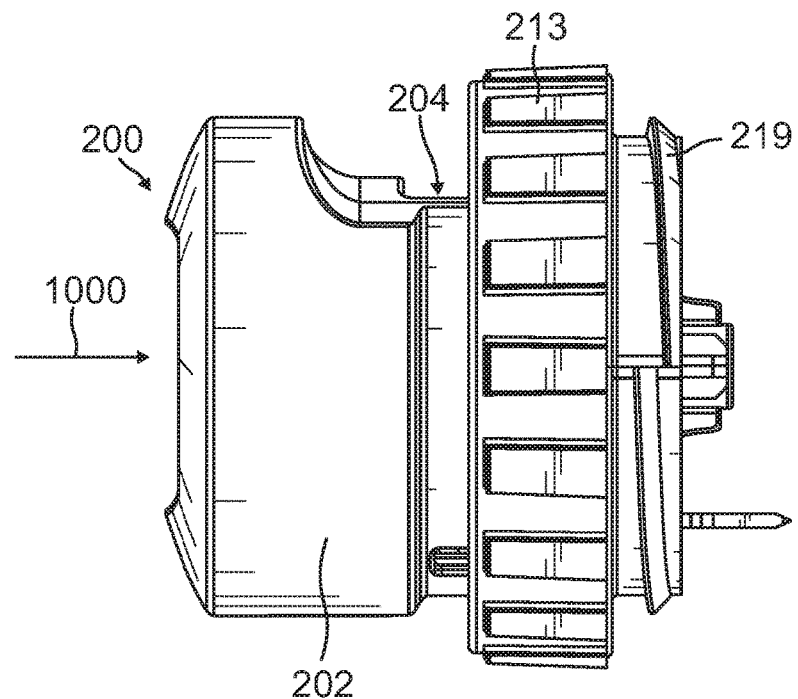
FIG. 4 is a side view of a desorber in an open position in accordance with an embodiment of the disclosure.
Figure 5:
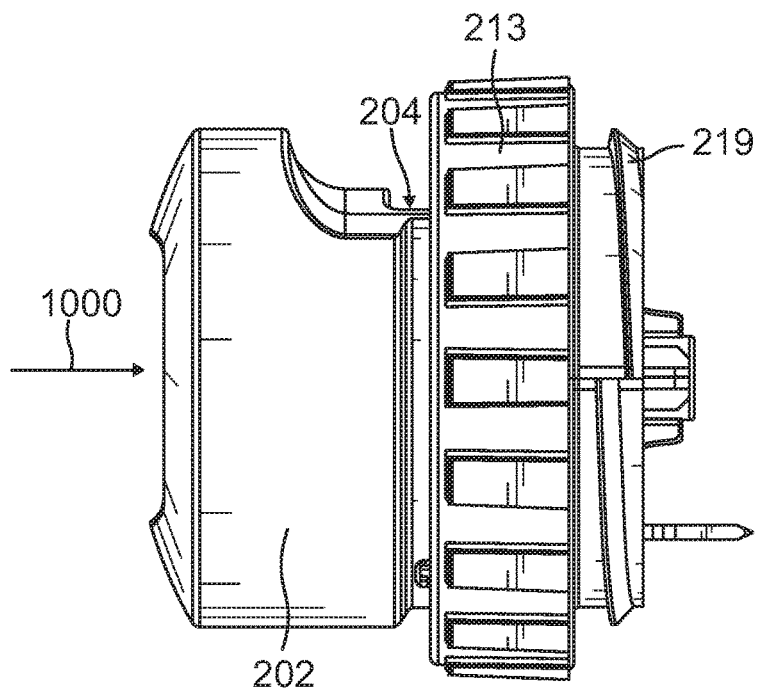
FIG. 5 is a side view of a desorber in a closed position in accordance with an embodiment of the disclosure.

Referring now to FIGS. 4 and 5, as discussed, desorber 200 includes a user operable cap 202 that may be selectively actuated by a user to transition the desorber 200 from an open position to a closed position. In this regard, FIG. 4 is a side view of desorber 200 in the open position and FIG. 5 is a side view of desorber 200 in the closed position in accordance with embodiments of the disclosure. While desorber 200 (including cap 202) is in the open position of FIG. 4, a user may depress cap 202 in the direction of arrow 1000. In response, cap 202 compresses a spring and slides in the direction of arrow 1000 to a closed position, thus causing desorber 200 to exhibit the closed position of FIG. 5. While the user continues to depress cap 202, desorber 200 remains in the closed position. When the user releases cap 202, it will slide back to the open position of FIG. 5 (e.g., in response to an expansion of the spring as further described herein).

Figure 6:
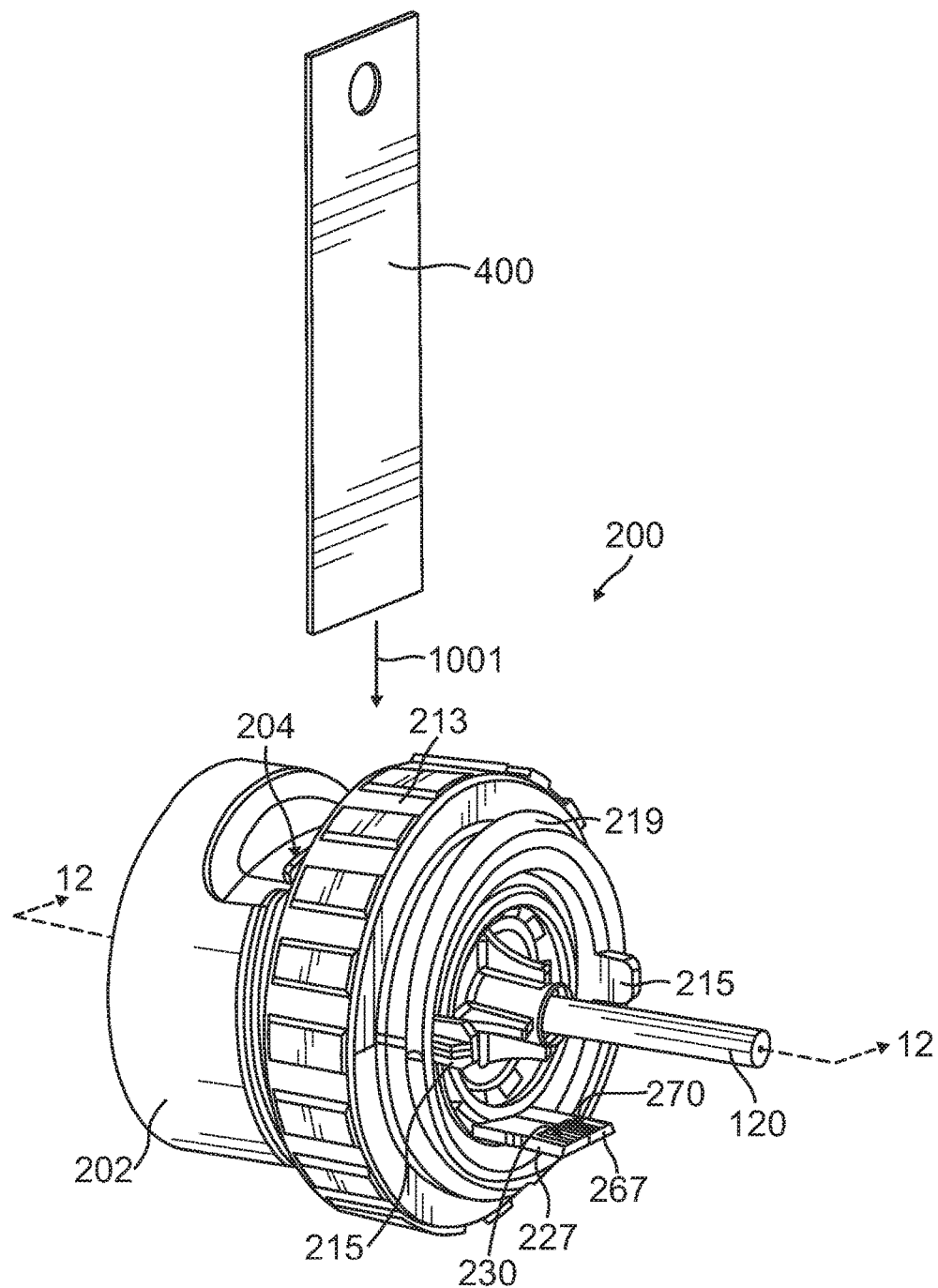
FIG. 6 is a perspective view of a desorber in an open position in accordance with an embodiment of the disclosure.

FIG. 6 is a perspective view of desorber 200 in the open position in accordance with an embodiment of the disclosure. As shown, a transfer tube 120 may be attached and held by desorber 200. As also shown, sample media 400 may be inserted into chamber 204 in the direction of arrow 1001.

Figure 7:
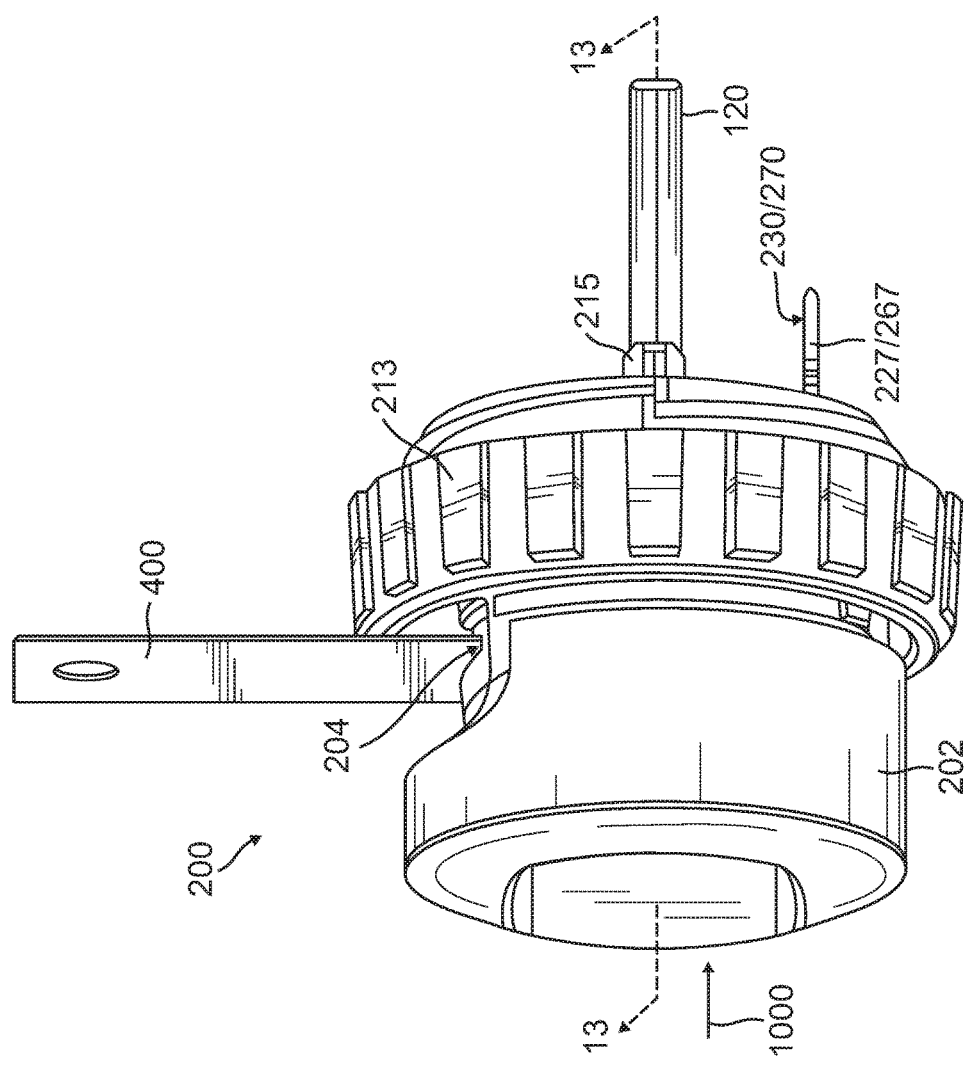
FIG. 7 is a perspective view of a desorber in a closed position in accordance with an embodiment of the disclosure.

FIG. 7 is a perspective view of desorber 200 in the closed position in accordance with an embodiment of the disclosure. In this case, sample media 400 has been inserted into chamber 204 and cap 202 has been actuated in the direction of arrow 1000. As a result, sample media 400 has been captured inside chamber 204 and is undergoing sampling and analysis.

FIG. 8 is a perspective view of desorber 200 separated into a main assembly 210 and an inlet subassembly 250 in accordance with an embodiment of the disclosure. In this regard, inlet subassembly 250 is configured to be inserted into main assembly 210 (e.g., inlet subassembly frame 254 may be inserted into and nest within main frame 214, see FIGS. 12 to 13).

FIGS. 9 to 11 illustrate various exploded views of main assembly 210 and inlet subassembly 250 in accordance with various embodiments of the disclosure. In particular, FIG. 9 is an exploded view of main assembly 210. As shown, main assembly 210 includes a cap 202, a spring 212, a threaded ring 213 having threads 219 thereon, a main frame 214 having flanges 215 extending therefrom, a slidable member subassembly 216, fasteners 211 and 217, a strain relief member 209 (e.g., a silicon tube providing strain relief for flexible circuit 226 further discussed herein), and a retainer 218.

Figure 10A:
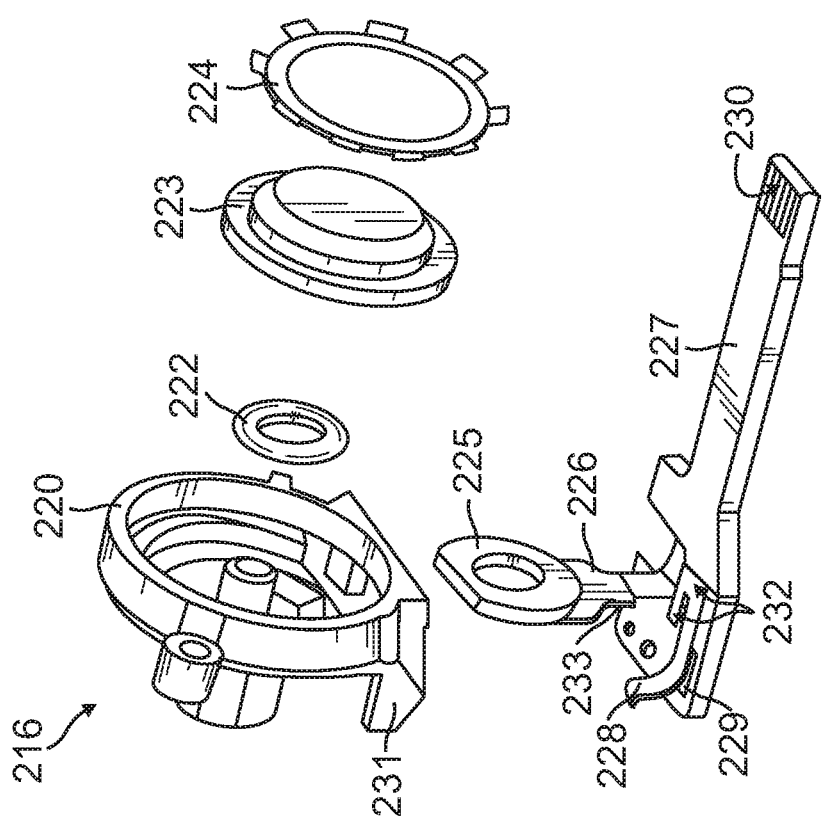

FIGS. 10A-B are exploded views of slidable member subassembly 216. As shown, slidable member subassembly 216 includes a slidable member 220 (e.g., also referred to as a sled) having an arm 231, an o-ring 222, a plate 223, a fastener 224, a circuit board 227 having electrical connections 230, a heater 225, a temperature sensor 233 (e.g., a thermistor), a flexible circuit 226, an electro-mechanical switch 228, and electrical contacts 229 and 232.

FIG. 11 is an exploded view of inlet subassembly 250. As shown, inlet subassembly 250 includes an inlet 252, o-rings 253, an inlet subassembly frame 254, a threaded receptacle 256, an o-ring 257, a retainer 258, a fastener 259, a heater 265, a temperature sensor 269 (e.g., a thermistor), a flexible circuit 266, a circuit board 267 having electrical connections 270, and a fastener 268.

Figure 12:
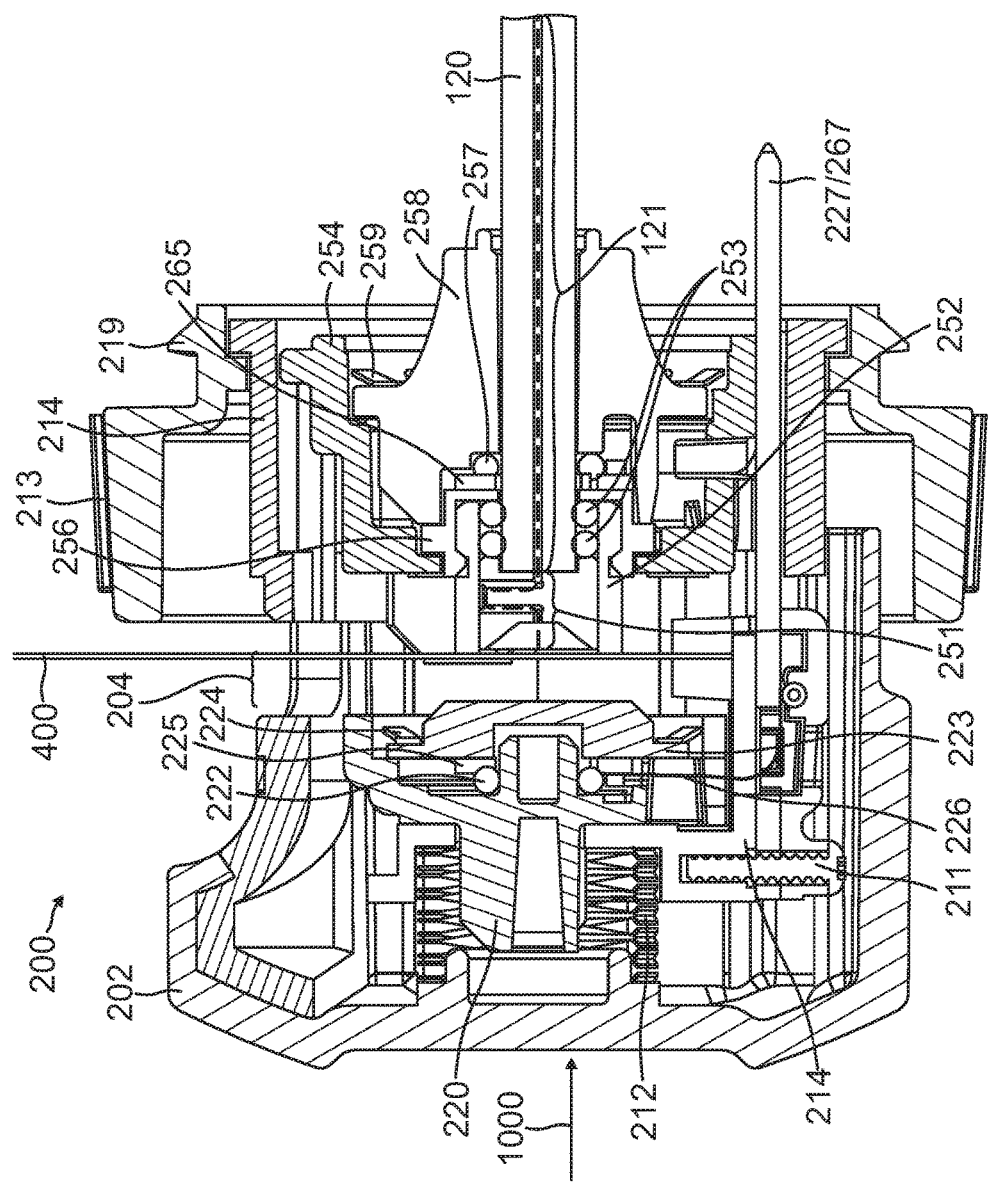
FIG. 12 is a cross-section view of a desorber in an open position taken at line 12-12 of FIG. 6 in accordance with an embodiment of the disclosure.
Figure 13:
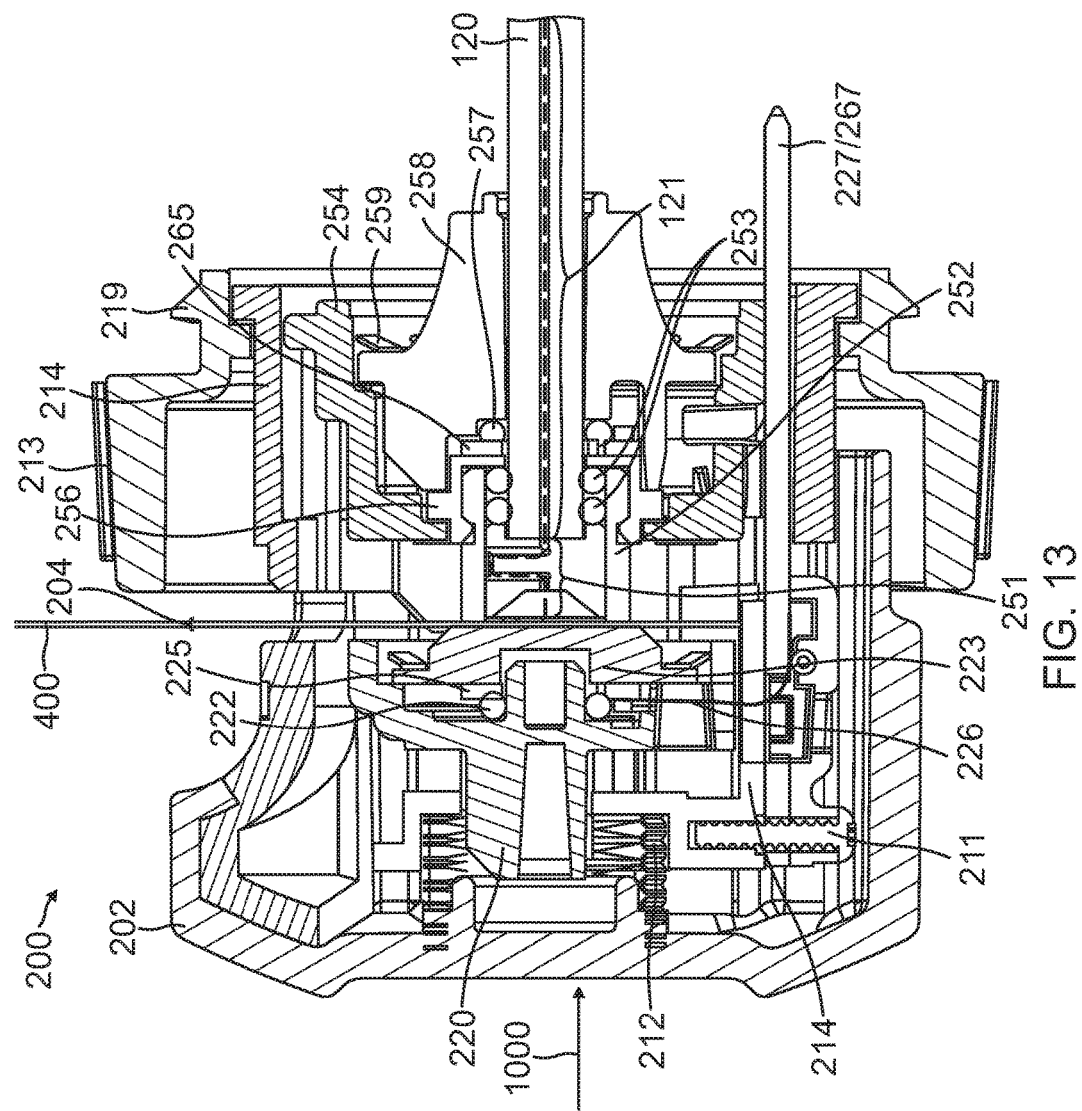
FIG. 13 is a cross-section view of a desorber in a closed position taken at line 13-13 of FIG. 7 in accordance with an embodiment of the disclosure.
Figure 14A:
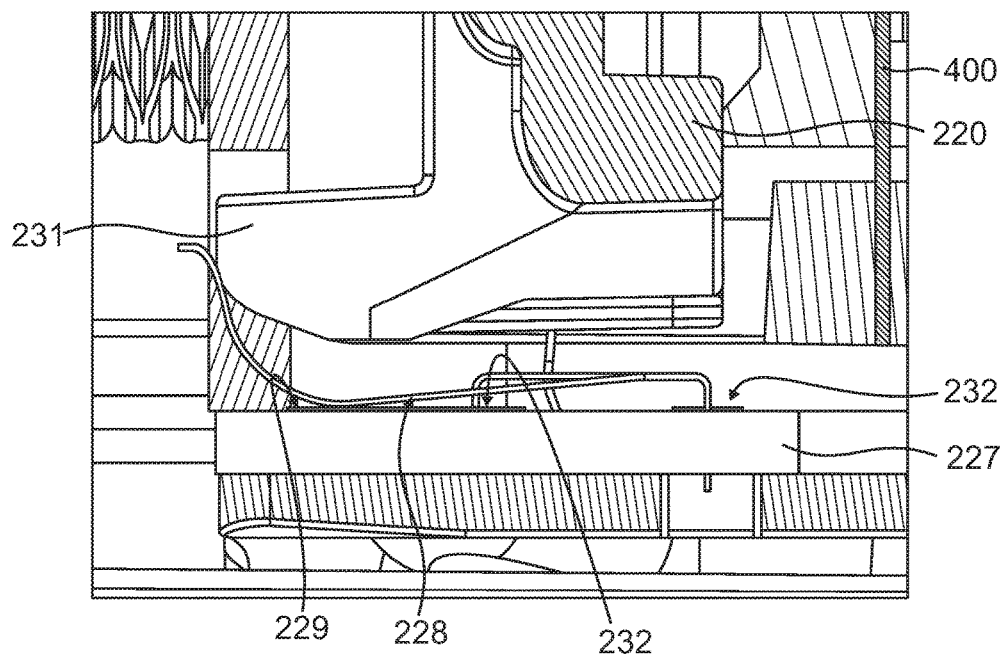
FIGS. 14A-B are various views of an electro-mechanical switch while a desorber is in an open position in accordance with an embodiment of the disclosure.
Figure 14B:
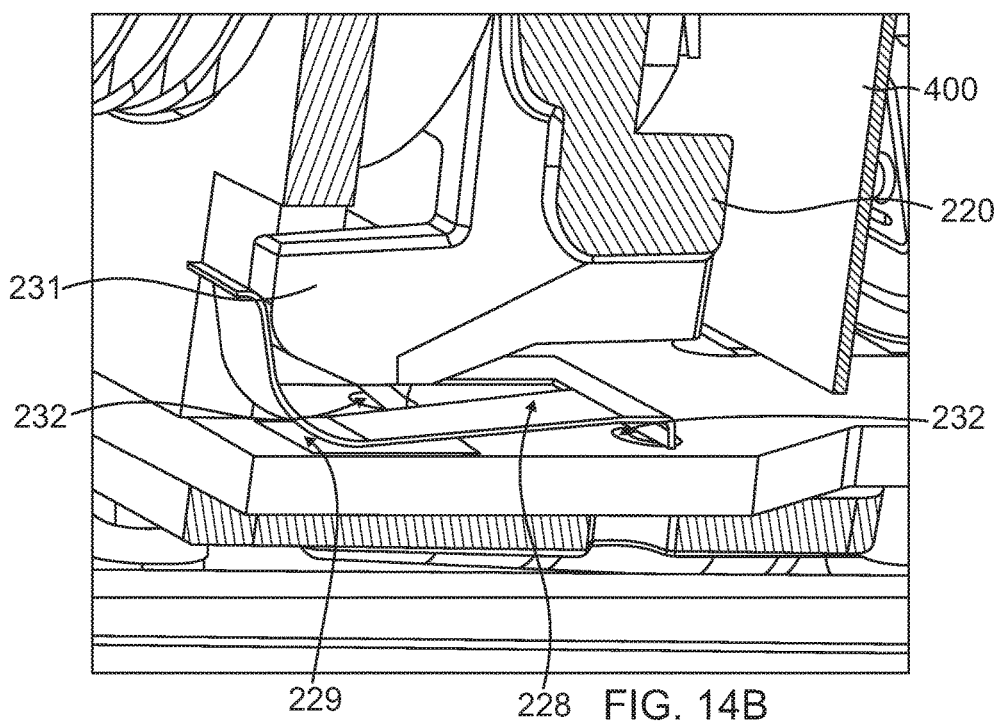
Figure 15A:
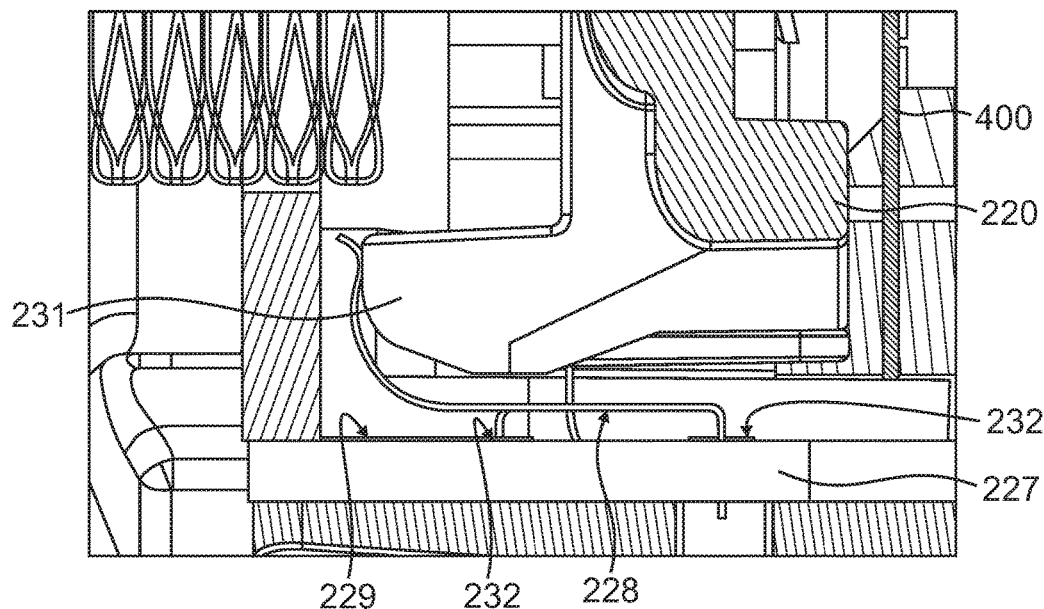
FIGS. 15A-B are various views of an electro-mechanical switch while a desorber is in a closed position in accordance with an embodiment of the disclosure.
Figure 15B:
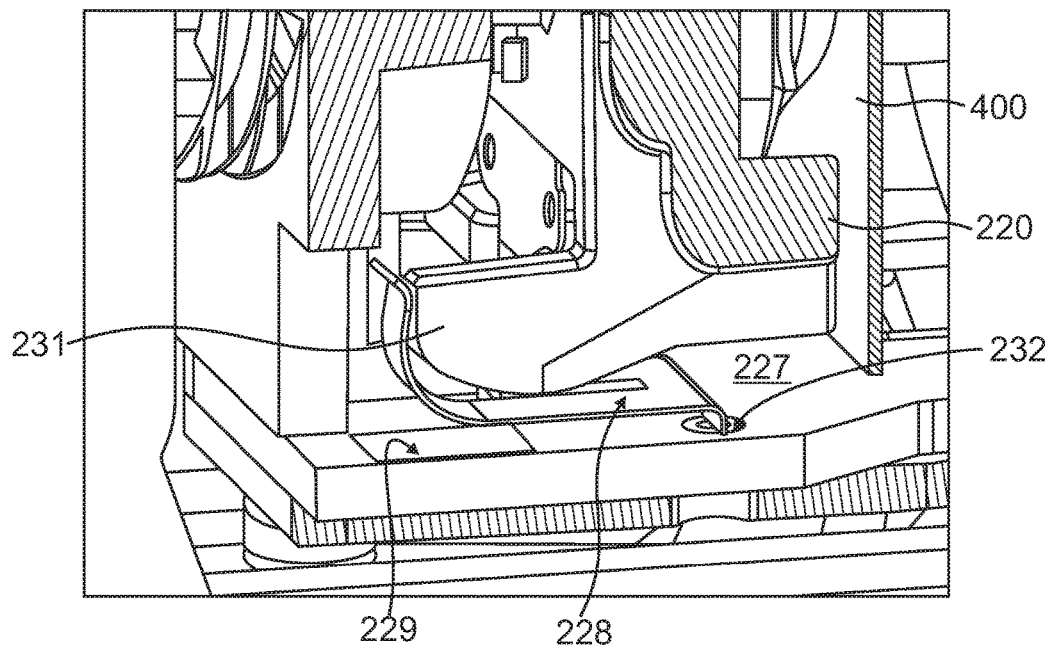
Figure 16:
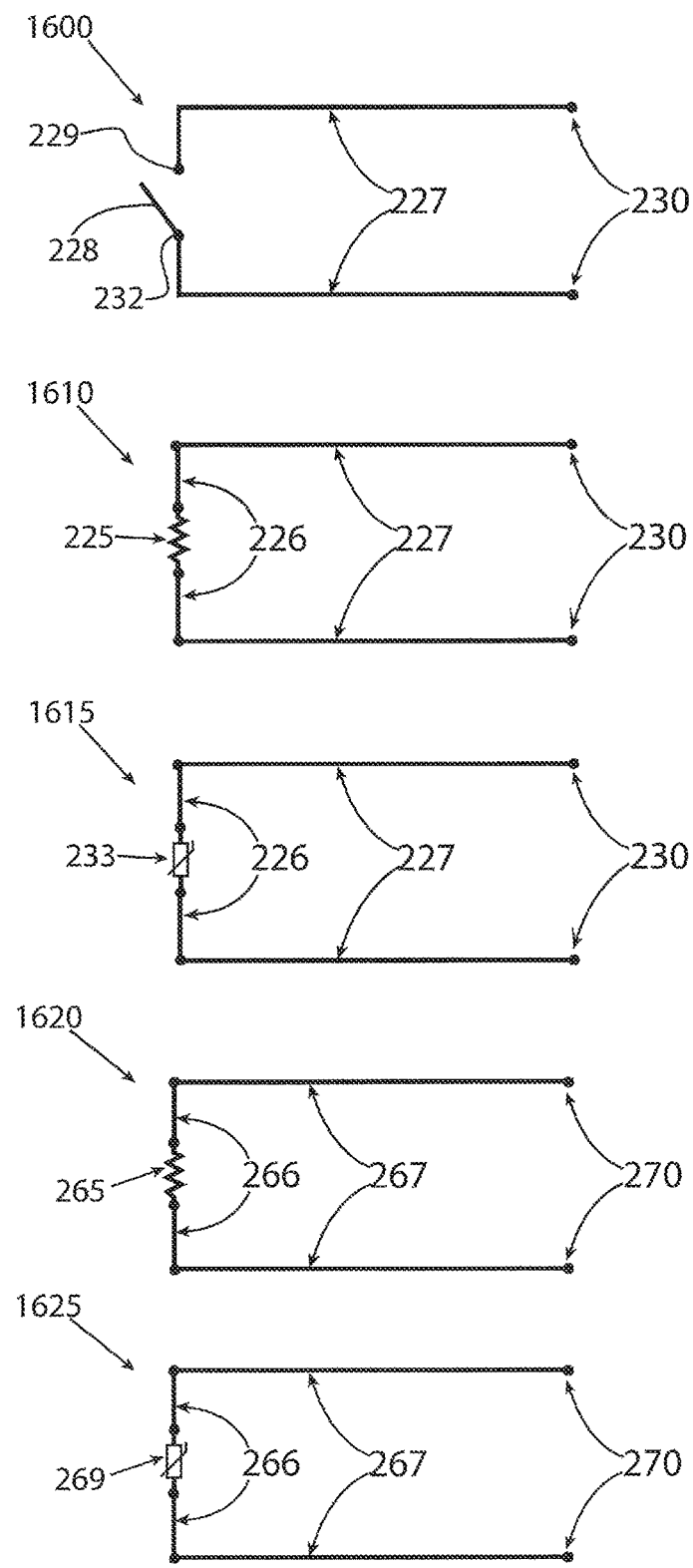
FIG. 16 illustrates several electrical circuits of a desorber in accordance with an embodiment of the disclosure.

Further details of the assembly and interoperation of the various components of desorber 200 will now be further described in relation to FIGS. 12 to 16. In this regard, FIG. 12 is a cross-section view of desorber 200 in the open position taken at line 12-12 of FIG. 6 in accordance with an embodiment of the disclosure. FIG. 13 is a cross-section view of desorber 200 in the closed position taken at line 13-13 of FIG. 7 in accordance with an embodiment of the disclosure. FIGS. 14A-B are various views of electro-mechanical switch 228 while desorber 200 is in an open position in accordance with an embodiment of the disclosure. FIGS. 15A-B are various views of electro-mechanical switch 228 while desorber 200 is in a closed position in accordance with an embodiment of the disclosure. FIG. 16 illustrates several electrical circuits 1600, 1610, 1615, 1620, and 1625 implemented by various components of desorber 200 in accordance with an embodiment of the disclosure.

Referring now to main assembly 210, spring 212 is disposed between cap 202 and main frame 214. In the absence of a user actuation, spring 212 resiliently biases cap 202 away from main frame 214 to maintain desorber 200 in the open position (see FIG. 12). When a user depresses cap 202 in the direction of arrow 1000, cap 202 compresses spring 212 and slides toward main frame 214 to transition desorber 200 to the closed position (see FIG. 13). In some embodiments, cap 202 may be constructed, for example, of one or more plastic materials to thermally insulate the user's finger from heaters 225/265 and/or other components of desorber 200.

Main frame 214 is held by threaded ring 213 which, as discussed, may be attached to main body 110 of device 100 by threads 219. Slidable member subassembly 216 nests substantially within main frame 214. Retainer 218 secures circuit board 227, and retainer 218 itself is secured to main frame 214 by fastener 211.

Referring now to slidable member assembly 216, it includes a slidable member 220 nested substantially within cap 202 and main frame 214 of main assembly 210. Slidable member 220 is secured to cap 202 by fasteners 217 and thus may slide forward (e.g., in the direction of arrow 1000) and backward (e.g., in an opposite direction of arrow 1000) with cap 202 as cap 202 is selectively depressed and released by a user. In this regard, although slidable member 220 is nested substantially within main frame 214, slidable member 220 may slide relative to main frame 214 as shown in FIGS. 12-13.

Slidable member 220 is further configured to hold a heater 225 (e.g., a ceramic heating element) nested therein. Heater 225 contacts a plate 223 (e.g., an aluminum plate) which is configured to conduct thermal energy received from heater 225 (e.g., heater 225 and plate 223 collectively provide a heater assembly). In this regard, an o-ring 222 is disposed between slidable member 220 and heater 225 to bias heater 225 against plate 223, thus permitting plate 223 to efficiently receive thermal energy from heater 225. A fastener 224 secures plate 223 to a front portion of slidable member 220.

Heater 225 is connected to circuit board 227 through flexible circuit 226 which may include a plurality of electrical traces (e.g., conductors) to pass electric power to heater 225 provided by main body 110 and received through electrical connections 113 and 230, circuit board 227, and flexible circuit 226. Similarly, temperature sensor 233 is connected to circuit board 227 through corresponding electrical traces of flexible circuit 226 to pass temperature signals from temperature sensor 233 to main body 110 through electrical connections 113 and 230, circuit board 227, and flexible circuit 226. In this regard, processor 160 may detect and monitor the temperature of heater 225 by such temperature signals.

Circuit board 227 is held in a fixed position by retainer 218 and the engagement of electrical connections 230 with electrical connections 113 of main body 110. However, heater 225 is disposed within slidable member 220 and therefore will move relative to circuit board 227 in response to a user actuation of cap 202. To help facilitate such movement, flexible circuit 226 may be implemented, for example, as a flexible circuit board (e.g., having a plastic substrate with electrical traces embedded therein and/or disposed thereon) configured to flexibly move with heater 225 while remaining attached to circuit board 227.

For example, comparing the open position of FIG. 12 with the closed position of FIG. 13, it is clear that circuit board 227 remains fixed, heater 225 translates forward in the direction of arrow 1000, and flexible member 226 will deform in response to the user actuation to remain connected to both heater 225 and circuit board 227.

Electro-mechanical switch 228 may be selectively opened and closed by slidable member 220 (e.g., transitioned between different switch states) in response to the user actuation of cap 202. In this regard, FIGS. 14A-B illustrate electro-mechanical switch 228, circuit board 227, and slidable member 220 while desorber 200 is in the open position.

Electro-mechanical switch 228 may be implemented, for example, by a flanged conductor secured to circuit board 227 at electrical contacts 232 and configured to selectively connect to another electrical contact 229 in response to the movement of slidable member 220. In this regard, slidable member 220 includes an arm 231 that biases against the flanged conductor to push electro-mechanical switch 228 downward into contact with electrical contact 229 to close an electrical circuit while desorber 200 is in the open position.

FIGS. 15A-B illustrate electro-mechanical switch 228, circuit board 227, and slidable member 220 while desorber 200 is in the closed position. In this case, slidable member 220 has been translated forward by the user actuation of cap 202. As a result, arm 231 of slidable member 220 has also moved and no longer pushes the flanged conductor of electro-mechanical switch 228 into contact with electrical contact 229, thus opening the electrical circuit while desorber 200 is in the closed position. Upon the user's release of cap 202, slidable member 220 will translate back to the position of FIGS. 14A-B, thus closing the electrical circuit again.

Although electro-mechanical switch 228 has been described as a normally closed switch (e.g., closed when no user actuation is performed), other embodiments are contemplated. For example, in some embodiments, electro-mechanical switch 228 may be implemented as a normally open switch with appropriate modifications made to slidable member 220 and/or arm 231.

Referring now to inlet subassembly 250, an inlet subassembly frame 254 is nested substantially within main frame 214 and secured to threaded ring 213. Threaded receptacle 256 is secured within inlet subassembly frame 254 and secures inlet 252 thereto. O-rings 253 secure transfer tube 120 within inlet 252. As shown in FIGS. 12-13, inlet 252 (e.g., also referred to as a sampling tip or an inlet member) provides a fluid path 251 (e.g., represented by a broken line in FIGS. 12-13) to pass vaporized samples from chamber 204 to transfer tube 120. Inlet 252 may be implemented, for example, in accordance with various embodiments set forth in International Patent Application Publication No. WO2015/054583 which is hereby incorporated by reference herein in its entirety. As also shown in FIGS. 12-13, transfer tube 120 provides another fluid path 121 (e.g., also represented by a broken line in FIGS. 12-13) connected to fluid path 251 to pass vaporized samples from inlet 252 to detector 124 of main body 110.

As discussed and shown in FIGS. 12-13, o-rings 253 secure transfer tube 120 within inlet 252. As also shown, inlet 252 is rigidly fixed relative to threaded ring 213 by the mechanical engagement of subframe 254 and threaded member 256 with inlet 252, and further by the mechanical engagement of subframe 254 with threaded ring 213. Therefore, by engaging threaded member 213 to main frame 210 by complementary threads 219 and 119, the fluid paths 251 and 121 provided by inlet 252 and transfer tube 120, respectively, can remain accurately aligned with main body 110 and detector 124 while still permitting complete detachment of desorber 200 from main body 110 when desired.

Heater 265 (e.g., a ceramic heating element) abuts threaded receptacle 256 and encircles transfer tube 120. In this regard, heater 265 may be operated to heat samples passed through fluid path 251. An opposite side of heater 265 abuts o-ring 257. A retainer 258 (e.g., a plastic retainer for thermal isolation) secures o-ring 257, heater 265, and threaded receptacle 256 to subframe 254. Fastener 259 in turn secures retainer 258 within desorber 200. In some embodiments, retainer 258 may be constructed, for example, of one or more plastic materials to thermally insulate the user's finger from heaters 225/265 and/or other components of desorber 200 (e.g., when desorber 200 is detached from main body 110).

Heater 265 is connected to circuit board 267 through flexible circuit 266 which may include a plurality of electrical traces (e.g., conductors) to pass electric power to heater 265 provided by main body 110 and received through electrical connections 116 and 270, circuit board 267, and flexible circuit 266. Similarly, temperature sensor 269 is connected to circuit board 267 through corresponding electrical traces of flexible circuit 266 to pass temperature signals from temperature sensor 269 to main body 110 through electrical connections 116 and 270, circuit board 267, and flexible circuit 266. In this regard, processor 160 may detect and monitor the temperature of heater 265 by such temperature signals.

In other embodiments, circuit 266 may be implemented by a fixed (e.g., rigid) circuit board and/or other types of conductive paths as appropriate. Circuit board 267 is secured to subframe 254 by fastener 268.

The electrical circuits implemented by the various components of desorber can be further understood with reference to FIG. 16. Circuit 1600 is used to connect electro-mechanical switch 228 to main body 110. In this regard, circuit board 227 provides conductive paths from electrical connections 230 to electro-mechanical switch 228. As shown, one end of electro-mechanical switch 228 is attached to one or more electrical contacts 232 of circuit board 227. Another end of electro-mechanical switch 228 is selectively connected to electrical contact 229 of circuit board 227 in response to the movement of arm 231 with slidable member 216. Thus, the operation of electro-mechanical switch 228 may provide a switching control signal at electrical connections 230 which may be received by appropriate components of main body 110 through electrical connections 113.

Circuit 1610 is used to connect heater 225 to main body 110. In this regard, circuit board 227 and flexible circuit 226 provide conductive paths from electrical connections 230 to heater 225. As shown, circuit 1615 similarly connects temperature sensor 233 to main body 110, for example, using additional electrical traces provided by the above-noted components discussed for circuit 1610.

Circuit 1620 is used to connect heater 265 to main body 110. In this regard, circuit board 267 and flexible circuit 266 provide conductive paths from electrical connections 270 to heater 265. As shown, circuit 1625 similarly connects temperature sensor 269 to main body 110, for example, using additional electrical traces provided by the above-noted components discussed for circuit 1620.

As discussed, the various electrical connections 230/270 of circuit boards 227/267 may interface with corresponding electrical connections 113/116 of main body 110 to interface electro-mechanical switch 228, heater 225, and heater 265 with appropriate components of main body 110. As shown in FIG. 16, in some embodiments, the electrical circuits 1600, 1610, 1615, 1620, and 1625 of desorber 200 may be implemented by passive components, thereby reducing weight and potential points of failure in desorber 200.

Figure 17:
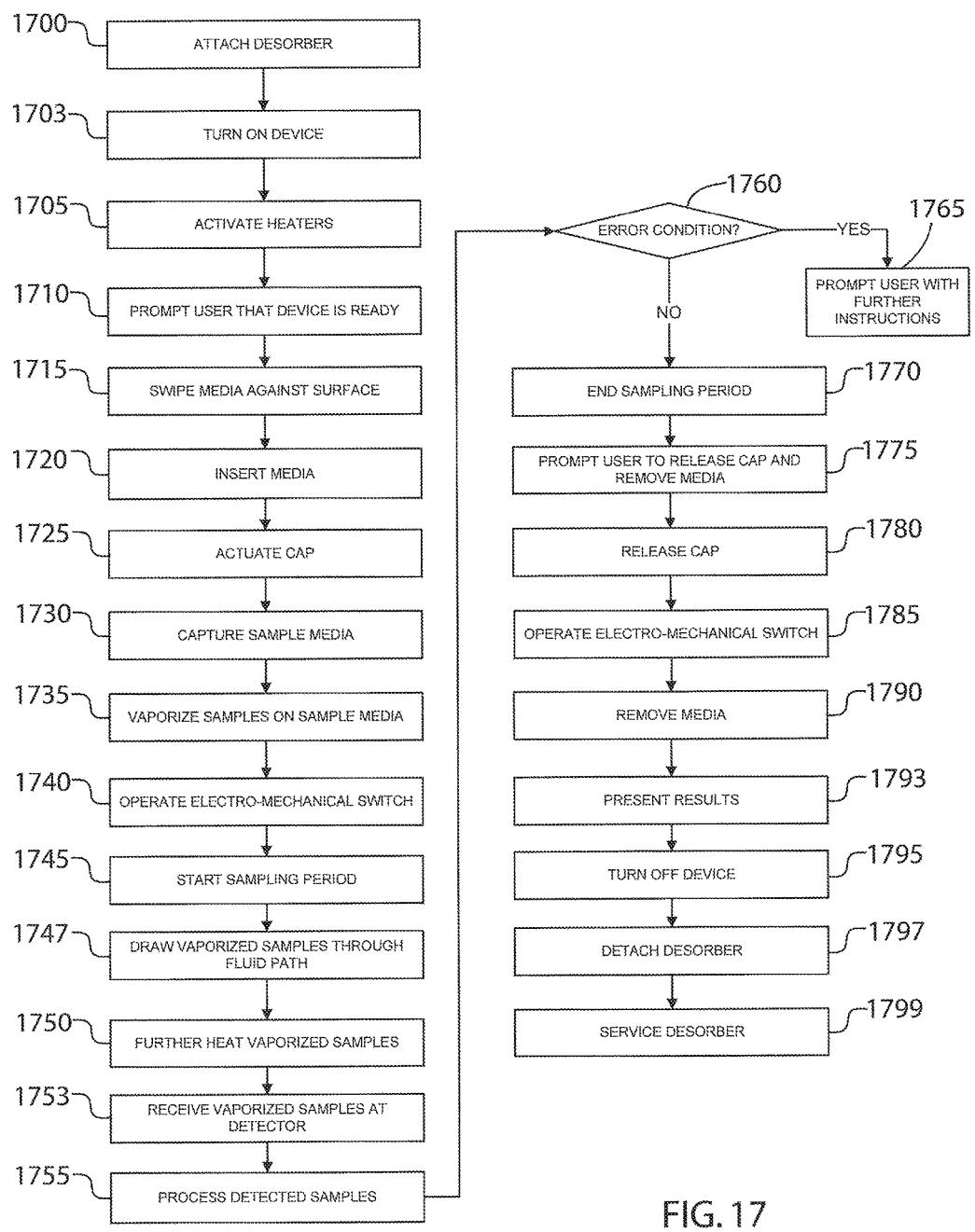
FIG. 17 illustrates a process of operating a sensor detector device in accordance with an embodiment of the disclosure.

Having described the various structural and electrical features of desorber 200 above, the overall operation of desorber 200 in relation to device 100 will be further described with regard to FIG. 17 which illustrates a process of operating device 100 in accordance with an embodiment of the disclosure.

In block 1700, a user attaches desorber 200 to main body 110 to prepare device 100 for user. In this regard, desorber 200 may have been previously detached for cleaning, servicing, replacement, transport, or other reasons. Block 1700 may be performed, for example, by inserting threaded ring 213 into aperture 117 of main body 110 and rotating threaded ring 213 to engage threads 119 and 219.

In block 1703, the user turns on device 100 (e.g., by operating user controls 150) to begin a startup sequence controlled by processor 160. In block 1705, as part of the startup sequence, main body 110 applies electric power to activate heaters 225 and 265 through circuits 1610 and 1620 as discussed. As a result, heaters 225 and 265 begin to warm up. In this regard, processor 160 monitors the temperature of heaters 225 and 265 by temperature signals provided by temperature sensors 233 and 269 as discussed.

After the heaters 225 and 265 have reached a warmed up steady state (e.g., as detected by processor 160 based on the temperature signals) and the startup sequence is complete, in block 1710, device 100 prompts the user that it is ready to begin receiving sample media 400 for processing. For example, device 100 may prompt the user by providing text or graphics on display 140, an audible signal by audio component 180, and/or other techniques as appropriate.

In block 1715, the user swipes sample media 400 against a surface to be tested, which causes chemical traces to be transferred from the test surface to the sample media 400. In block 1720, the user inserts the sample media 400 into chamber 204. For example, as shown in FIG. 12, while desorber 200 is in the open position, the inserted sample media 400 may extend into chamber 204 and rest on an inside surface of main frame 214. As also shown in FIG. 12, sample media 400 is positioned in proximity to or abutment with inlet 252, but is displaced from plate 223 while desorber 200 is in the open position.

In block 1725, the user actuates (e.g., depresses) cap 202 in the direction of arrow 1000 to transition desorber 200 from the open position of FIG. 12 to the closed position of FIG. 13. In this regard, cap 202 slides forward in the direction of arrow 1000, thus closing chamber 204 (e.g., chamber 204 is closed in FIG. 13 as denoted by the small brace of label 204 corresponding to the thickness of sample media 400). The user may continue to depress cap 202 and thus maintain desorber 200 in the closed position until device 100 prompts the user to release the cap 202 in block 1775.

As previously discussed, the user actuation causes cap 202 to slide forward in the direction of arrow 1000, compress spring 212, and also move slidable member 220 in the direction of arrow 1000. Such movement triggers the operations of blocks 1730, 1735, 1740, and 1745. Although blocks 1730, 1735, 1740, and 1745 are illustrated as sequential blocks, they may occur substantially simultaneously and/or in different orders in other embodiments.

In block 1730, sample media 400 is captured between plate 223 and inlet 252. In this regard, because heater 225, o-ring 222, and plate 223 are all secured to slidable member 220 by fastener 224, the movement of slidable member 220 will bring plate 223 into contact with sample media 400 and force sample media 400 against inlet 252 as shown in FIG. 13. As discussed and also shown in FIG. 13, the use of flexible member 226 permits heater 225 to move with slidable member 220.

In block 1735, plate 223 begins vaporizing samples on sample media 400. As discussed, plate 223 will be heated by thermal energy provided by heater 225. As a result, plate 223 will heat sample media 400 to begin vaporizing samples (e.g., chemical traces) picked up by sample media 400 as a result of the user's swiping previously performed in block 1715. Also in block 1735, heater 265 of inlet subassembly 250 also operates to vaporize the samples.

In block 1740, as slidable member 220 moves in response to the user actuation of cap 202, it will cause arm 231 to release electro-mechanical switch 228 from contact 229, thus opening electro-mechanical switch 228. As discussed, the operation of electro-mechanical switch 228 may be received by various components of main body 110. For example, processor 160 may detect the switching of electro-mechanical switch 228 as a control signal to begin a sampling process.

From blocks 1745 to 1770, a chemical analysis process is performed over a predetermined sampling period during which time vaporized samples from sample media 400 are detected to determine their chemical composition. In block 1745, processor 160 starts the sampling period, for example, in response to the control signal provided by electro-mechanical switch 228. In block 1747, pump 122 draws the vaporized samples through the fluid path 251 provided by inlet 252 and transfer tube 120, and continues to operate during the sampling period. In block 1750, as the vaporized samples pass through fluid path 251, they are further heated by heater 265. In block 1753, detector 124 receives the vaporized samples. In block 1755, detector 124 processes the vaporized samples to determine their chemical composition using various techniques as discussed above.

During the analysis process of blocks 1745 to 1770, one or more error conditions may occur. For example, a user may release cap 202 prematurely (e.g., which may be detected by main body 110 receiving a control signal generated by a premature closing of electro-mechanical switch 228), one or more components may malfunction, and/or other problems may arise. In block 1760, if such an error condition is detected, then the process continues to block 1765 where device 100 prompts the user (e.g., in accordance with the techniques described herein) with further instructions (e.g., to re-actuate cap 202, restart device 100, service desorber 200, and/or other appropriate instructions). Otherwise, the process continues to block 1770. Although block 1760 is illustrated sequentially after block 1755, the detection of error condition may be performed at any time during the process of FIG. 17 in various embodiments.

In block 1770, processor 160 ends the sampling period, for example, after an associated time period has expired. In block 1775, device 100 prompts the user (e.g., in accordance with the techniques described herein) to release cap 202 and remove sample media 400.

In block 1780, the user releases cap 202 which causes desorber 200 to return to the open position, thus opening chamber 204. In this regard, spring 212 expands which causes cap 202 to slide back to the orientation shown in FIG. 12. As discussed, slidable member 220 is secured to cap 202 by fasteners 217 and therefore also slides back with cap 202 to the orientation shown in FIG. 12. Because plate 223 is also secured to slidable member 220, it will be removed from sample media 400, leaving sample media 400 free to be removed from chamber 204.

In block 1785, the sliding back of slidable member 220 causes arm 231 to engage electro-mechanical switch 228 with contact 229, thus closing electro-mechanical switch 228. Such operation may generate a control signal which informs processor 160 that desorber 200 has returned to the open position. In block 1790, the user removes sample media 400 from chamber 204.

In block 1793, device 100 presents the results of the analysis process to the user. For example, device 100 may identify one or more detected chemicals and may provide such information to the user by way of display 140 and/or audio component 180.

In block 1795, the user turns off device 100 (e.g., by operating user controls 150). In block 1797, the user detaches desorber 200 from main body 110, for example, by rotating threaded ring 213 to disengage threads 119 and 219, and removing threaded ring 213 from aperture 117 of main body 110. In block 1799, the user services desorber 200 while detached from main body 110 if needed. In this regard, the implementation of desorber 200 as a detachable unit permits the user to clean, replace, or otherwise service desorber in a convenient manner without requiring disassembly of main body 110.

In view of the present disclosure, it will be appreciated that a desorber of a sensor detector device may be implemented with convenient and user controllable manual operation. As discussed, the desorber may be implemented in a modular fashion such that the desorber may be selectively attached to, and detached from, a main body of the sensor detector device. Moreover, through the use of the various described electrical connections and mechanical engagements, the desorber may be reliably interfaced with the main body of the sensor detector device and used to trigger sampling operations for chemical analysis processes performed therewith.

Where applicable, various embodiments provided by the present disclosure can be implemented using hardware, software, or combinations of hardware and software. Also where applicable, the various hardware components and/or software components set forth herein can be combined into composite components comprising software, hardware, and/or both without departing from the spirit of the present disclosure. Where applicable, the various hardware components and/or software components set forth herein can be separated into sub-components comprising software, hardware, or both without departing from the spirit of the present disclosure. In addition, where applicable, it is contemplated that software components can be implemented as hardware components, and vice-versa.

Software in accordance with the present disclosure, such as program code and/or data, can be stored on one or more non-transitory machine readable mediums. It is also contemplated that software identified herein can be implemented using one or more general purpose or specific purpose computers and/or computer systems, networked and/or otherwise. Where applicable, the ordering of various steps described herein can be changed, combined into composite steps, and/or separated into sub-steps to provide features described herein.

Embodiments described above illustrate but do not limit the invention. It should also be understood that numerous modifications and variations are possible in accordance with the principles of the present invention. Accordingly, the scope of the invention is defined only by the following claims.

We claim:

1. A device comprising:
    a desorber comprising:
        an inlet comprising a fluid path configured to receive samples from sample media,
        a cap configured to slide toward the inlet in response to a manual actuation of the cap performed by a user to transition the desorber from an open position to a closed position, and a heater configured to slide with the cap toward the inlet in response to the user actuation and provide the samples from the sample media while the desorber is in the closed position;

a detector configured to be in fluid communication with the inlet to receive the samples and process the samples to determine their composition; and a transfer tube secured to the desorber and connected to the fluid path to pass the samples, wherein the samples are vaporized samples, wherein the detector is a chemical detector.

2. The device of claim 1, wherein the device is a sensor detector device further comprising a main body, the desorber further comprising a threaded ring configured to selectively attach the desorber to the main body.

3. The device of claim 1, the desorber further comprising a spring configured to compress in response to the user actuation to permit the cap and the heater to slide toward the inlet and decompress in response to a release of the cap by the user to cause the cap to slide away from the inlet.

4. The device of claim 1, wherein the cap is constructed of plastic to insulate the user from the heater.

5. The device of claim 1, the desorber further comprising a plate disposed between the heater and the inlet and configured to slide with the heater to capture the sample media between the plate and the inlet while the desorber is in the closed position.

6. The device of claim 1, the desorber further comprising:
a fixed electrical connection configured to receive electric power;
a flexible circuit connected between the fixed electrical connection and the heater; and
wherein the flexible circuit is configured to deform as the heater slides in response to the user actuation and to pass the electric power to the heater while the desorber is in the open and closed positions.

7. The device of claim 1, wherein the heater is a first heater, the desorber further comprising a second heater in a fixed position relative to the inlet and configured to heat the samples passed through the fluid path.

8. A device comprising:
a desorber comprising:
an inlet comprising a fluid path configured to receive samples from sample media,
a cap configured to slide toward the inlet in response to a manual actuation of the cap performed by a user to transition the desorber from an open position to a closed position,
a heater configured to slide with the cap toward the inlet in response to the user actuation and provide the samples from the sample media while the desorber is in the closed position, and
a slidable member secured to the cap and configured to slide with the cap in response to the user actuation, wherein the heater is secured to the slidable member; and
a detector configured to be in fluid communication with the inlet to receive the samples and process the samples to determine their composition.

9. The device of claim 1, the desorber further comprising:
an electro-mechanical switch configured to transition from a first switch state to a second switch state in response to the user actuation of the cap; and
electrical connections configured to pass a control signal in response to the transition to trigger a sampling period.

10. A method of operating the device of claim 1, the method comprising:
applying the manual actuation of the cap to begin a sampling period; and
releasing the cap after the sampling period has ended.

11. A method of manufacturing the device of claim 1, the method comprising:
providing a main assembly comprising the cap and the heater;
providing a subassembly comprising the inlet; and
inserting the subassembly into the main assembly.

12. A method comprising:
receiving sample media in a desorber of a sensor detector device comprising a main body, the desorber, and a detector, wherein the desorber is configured to be selectively attached to the main body, wherein the desorber comprises a cap, an inlet, and a heater, wherein the detector is disposed in the main body;
receiving a manual actuation of the cap performed by a user to transition the desorber from an open position to a closed position;
sliding the cap and the heater toward the inlet in response to the user actuation;
operating the heater to provide samples from the sample media;
passing the samples through a fluid path of the inlet;
passing the samples from the fluid path of the inlet through a transfer tube to the detector; and
processing the samples using the detector to determine their composition.

13. The method of claim 12, further comprising:
presenting the composition to the user, wherein the samples are vaporized samples, wherein the detector is a chemical detector.

14. The method of claim 12, the method further comprising attaching the desorber to the main body by a threaded ring of the desorber.

15. The method of claim 12, further comprising:
compressing a spring of the desorber in response to the user actuation to permit the cap and the heater to slide toward the inlet; and
decompressing the spring in response to a release of the cap by the user to cause the cap to slide away from the inlet.

16. The method of claim 12, further comprising sliding a plate of the desorber with the heater to capture the sample media between the plate and the inlet while the desorber is in the closed position.

17. The method of claim 12, further comprising:
passing electric power received from a fixed electrical connection to the heater by a flexible circuit while the desorber is in the open position;
deforming the flexible circuit in response to the user actuation; and
continuing the passing while the desorber is in the open position.

18. The method of claim 12, wherein the heater is a first heater, the method further comprising:
heating, by a second heater of the desorber in a fixed position relative to the inlet, the samples passed through the fluid path.

19. The method of claim 12, further comprising:
transitioning an electro-mechanical switch of the desorber from a first state to a second state in response to the user actuation of the cap;

passing a control signal in response to the transition; and
triggering a sampling period by the control signal.

\* \* \* \* \*